(12) United States Patent
Kirwan, Jr. et al.

(10) Patent No.: US 7,402,754 B2
(45) Date of Patent: Jul. 22, 2008

(54) INTEGRAL ELECTRICALLY CONDUCTING CORD AND LUMEN

(75) Inventors: Lawrence T. Kirwan, Jr., Pembroke, MA (US); John P. Ariola, Jr., Norton, MA (US)

(73) Assignee: Kirwan Surgical Products, Inc., Marshfield, MA (US)

( * ) Notice: Subject to any disclaimer, the term of this patent is extended or adjusted under 35 U.S.C. 154(b) by 1029 days.

(21) Appl. No.: 10/426,345

(22) Filed: Apr. 30, 2003

(65) Prior Publication Data

US 2004/0220561 A1   Nov. 4, 2004

(51) Int. Cl.
*H01B 7/00* (2006.01)

(52) U.S. Cl. .............................. 174/110 R; 174/113 R; 174/113 C

(58) Field of Classification Search ............. 174/110 R, 174/111, 36; 138/108, 111, 115
See application file for complete search history.

(56) References Cited

U.S. PATENT DOCUMENTS

| | | | | |
|---|---|---|---|---|
| 2,286,462 A * | 6/1942 | Chaffin | ......................... | 604/43 |
| 3,580,983 A | 5/1971 | Jackson | ......................... | 174/47 |
| 4,223,969 A | 9/1980 | Gatturna | ......................... | 339/15 |
| 4,399,319 A * | 8/1983 | Zinn | ......................... | 174/47 |
| 4,925,452 A * | 5/1990 | Melinyshyn et al. | ......... | 604/284 |
| 5,069,254 A * | 12/1991 | Vogelsang | ................... | 138/111 |
| 5,236,016 A * | 8/1993 | Vogelsang | ................... | 138/115 |
| 5,334,167 A * | 8/1994 | Cocanower | ................. | 604/523 |
| 5,336,220 A * | 8/1994 | Ryan et al. | ..................... | 604/22 |
| 5,417,690 A | 5/1995 | Sennett et al. | ................. | 606/61 |
| 5,947,953 A * | 9/1999 | Ash et al. | ..................... | 604/508 |
| 5,968,087 A | 10/1999 | Hess et al. | ................... | 607/127 |
| 5,989,249 A | 11/1999 | Kirwan, Jr. | ................... | 606/50 |
| 6,228,084 B1 | 5/2001 | Kirwan, Jr. | ................... | 606/52 |
| 6,363,273 B1 | 3/2002 | Mastrorio et al. | ........... | 600/434 |
| 6,367,510 B1 | 4/2002 | Carlson | ....................... | 138/121 |
| 6,406,476 B1 | 6/2002 | Kirwan, Jr. et al. | ........... | 606/50 |
| 6,434,430 B2 | 8/2002 | Borgersen et al. | ........... | 607/122 |
| 7,018,374 B2 * | 3/2006 | Schon et al. | ................. | 604/544 |
| 2002/0183824 A1 | 12/2002 | Borgersen et al. | ........... | 607/122 |

FOREIGN PATENT DOCUMENTS

JP    07-245023 A  *  9/1995
WO    WO 01/01535 A1 *  1/2001

OTHER PUBLICATIONS

"Rhoton Non-Stick Mirror Finish Bipolar Forceps", Codman brochure, no date.
"Coagulators Irrigation Module", Codman brochure, no date.

* cited by examiner

*Primary Examiner*—William H Mayo, III
(74) *Attorney, Agent, or Firm*—Weingarten, Schurgin, Gagnebin & Lebovici LLP

(57) ABSTRACT

A cable assembly interconnects an electrosurgical instrument and source equipment for power and fluid transfer. The cable assembly includes a unitary tubular assembly forming a lumen(s) and an insulating sheath(s) for an electrically conducting cord that are integrally interconnected via a web arrangement in a continuum of material. The web arrangement has a thickness sufficient to allow the lumen(s) and sheath(s) to be pulled apart upon application of a pulling force in a direction transverse to the direction of elongation of the tubular assembly.

10 Claims, 3 Drawing Sheets

INTEGRAL ELECTRICALLY CONDUCTING CORD AND LUMEN

CROSS REFERENCE TO RELATED APPLICATIONS

N/A

STATEMENT REGARDING FEDERALLY SPONSORED RESEARCH OR DEVELOPMENT

N/A

BACKGROUND OF THE INVENTION

A variety of electrosurgical devices are available for performing different surgical procedures. For example, coagulation procedures require an instrument that is capable of coagulating tissue to stop or minimize the flow of blood at the surgical site. Such instruments may also be capable of flushing an irrigation solution into the area where the surgeon is working to remove bits of tissue or blood. In other alternatives, these instruments may be capable of aspirating fluids from the site. Such fluids include liquids, such as saline solution or blood, and gases, such as smoke or air.

For example, electrosurgical forceps have a pair of blades that are used to grasp and coagulate tissue. The forceps may be monopolar or bipolar. In monopolar forceps, one or both of the blades form an electrode in electrical communication with an electrical generator. Current flows from the active electrode through the patient's tissue to a dispersive electrode in contact with the patient's skin, which may be at some distance from the forceps, and back to the generator. In bipolar forceps, each blade of the pair comprises an electrode in communication with the electrical generator.

In some forceps, an irrigation channel is formed along one or both of the blades to allow an irrigation fluid, such as saline solution, to flow through the channel and out the outlet near the tip of the blades to flush bits of tissue or blood away from the area where the surgeon is working. See, for example, U.S. Pat. No. 6,228,084.

In another known type of bipolar coagulating instrument, a pair of electrodes is arranged coaxially. A suction channel is provided along the central axis to draw fluids away from the surgical site. See, for example, U.S. Pat. Nos. 5,989,249 and 6,406,476.

In instruments that provide both coagulation capabilities and irrigation or aspiration capabilities, the instrument must be connected to both an electrical generator via an electrically conducting cord and to a fluid pump or vacuum compressor for irrigation or aspiration via a lumen. The electrically conducting cord is formed with a pair of copper wires each coaxially surrounded by an outer insulation. The fluid tubing for the lumen is typically formed from a suitable plastic material. It is known to form an electrically conducting cord and a lumen into a cable assembly by bonding the cord and lumen together with a glue or other bonding solution.

SUMMARY OF THE INVENTION

The present invention relates to a dual-function cable assembly in which an electrically conducting cord is integrally formed with an additional lumen or lumens. The cable assembly carries electrical energy from a source to an electrosurgical instrument. In addition, the cable assembly has the ability to irrigate or aspirate from the instrument end via a fluid or vacuum source through the lumen or lumens integrally connected to the electrical cord.

The electrical cord and the lumen(s) are arranged in a compact configuration and are interconnected by an integrally formed web arrangement that is sufficiently strong to hold the cord and lumen(s) together but is sufficiently thin to allow the lumen to be "unzipped" from the cord for a distance to facilitate connections at the source end or the instrument end.

DESCRIPTION OF THE DRAWINGS

The invention will be more fully understood from the following detailed description taken in conjunction with the accompanying drawings in which.

DETAILED DESCRIPTION OF THE INVENTION

Figure 1:
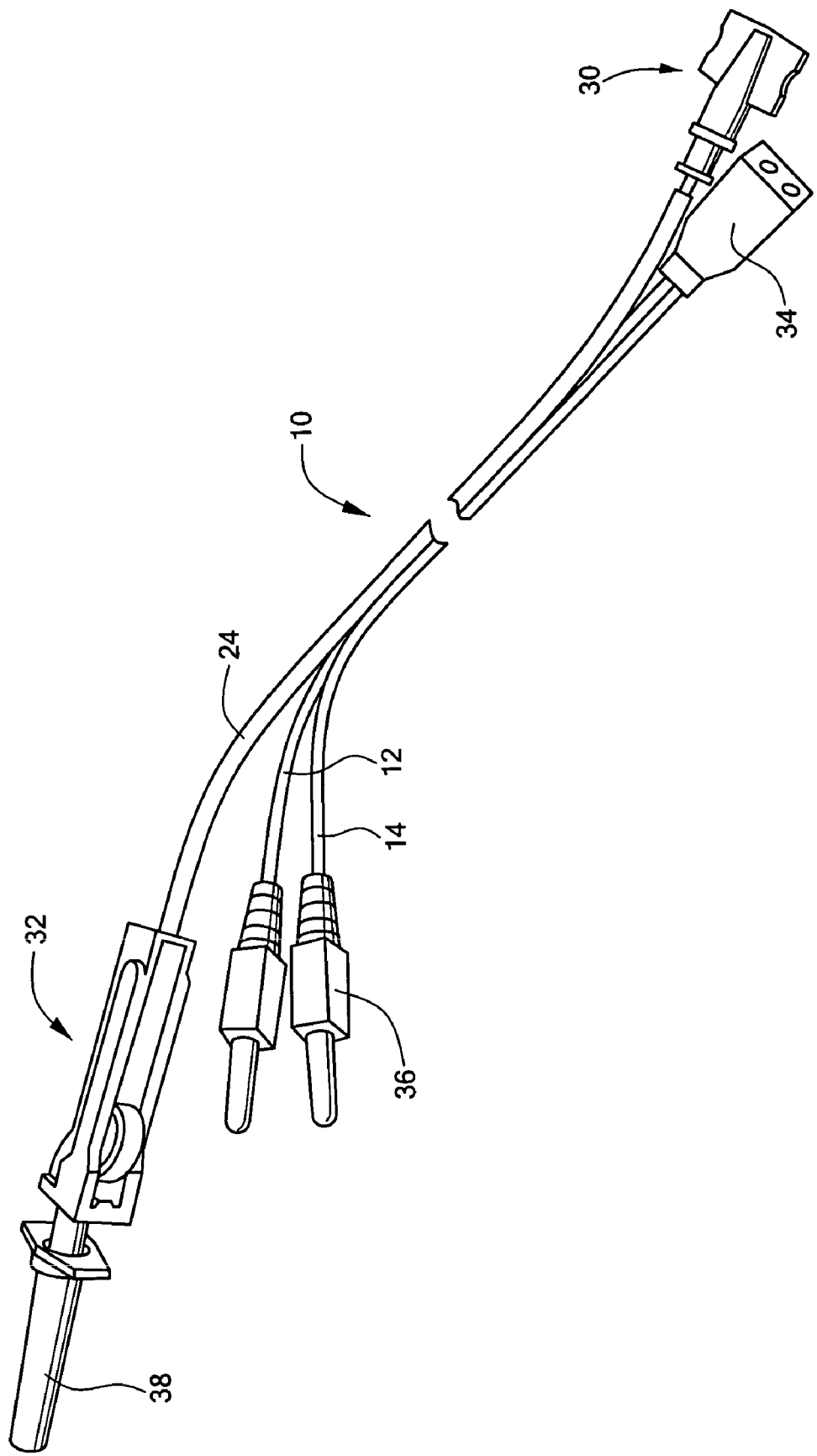
FIG. 1 is an isometric view of a cable assembly according to the present invention.
Figure 2:
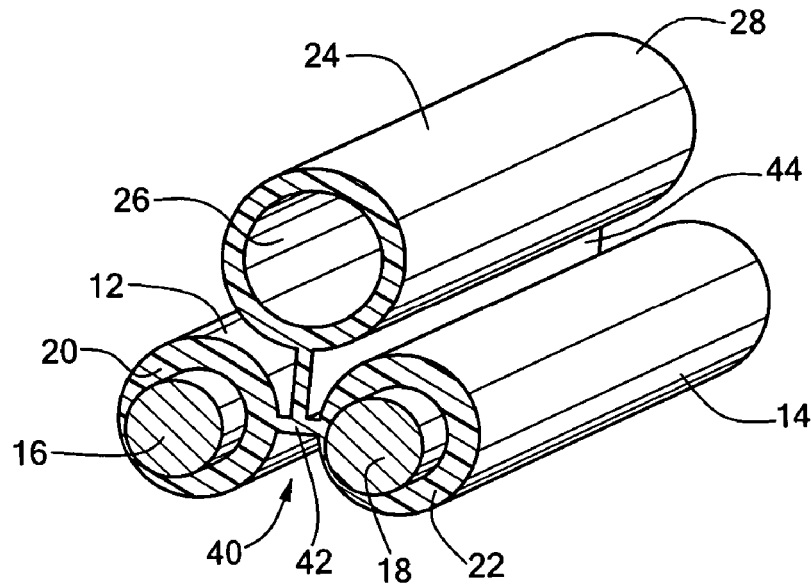
FIG. 2 is a partial cross-sectional view of the cable assembly of FIG. 1.

A first embodiment of a cable assembly according to the present invention is illustrated in FIGS. 1 and 2. The cable assembly 10 includes one or more electrically conducting cords 12, 14, each having a copper or other electrically conducting wire 16, 18 enclosed within an insulating sheath 20, 22. One or more lumens 24 are provided in the form of tubing 28 defining a fluid passage 26 therethrough. The electrically conducting cords and the lumen(s) extend longitudinally from a source end 30 to an instrument end 32. The cords and lumen(s) are attachable via suitable fittings at the source end to suitable source equipment (not shown), such as an electrical generator for the electrical cords and a fluid or vacuum source, e.g., a fluid pump or vacuum compressor, for the lumen(s). Similarly, the cords and lumen(s) are attachable via suitable fittings at the instrument end to an electrosurgical instrument. The lumen, or lumens, allows, for instance, irrigation using saline to the electrosurgical site through the instrument connected at the instrument end of the cable assembly. The lumen may also be used for aspiration from a site of either a liquid (for example, saline or blood) or a gas (for example, air or smoke).

The fittings 34 at the source end of the electrical conducting cords include any appropriate termination that connects to the electrical generator, such as banana pin connectors, phone jack connectors, and the like. The fittings 36 at the instrument end include any appropriate termination that connects to the instrument; typically, standard diameter pins, such as 0.073 inches, are provided. Similarly, the ends of the lumen(s) can be terminated in various ways to make the connections to the appropriate instrument and source. Typically, luer taper fittings 38 are provided for connection to medical devices.

The two insulating sheaths 20, 22 and the tubing 28 of the lumen 24 are formed of a flexible plastic material. The two insulating sheaths and the tubing of the lumen are integrally connected to each other via a web arrangement 40 in a continuum of material to form a single, unitary tubular assembly. In the embodiment illustrated in FIG. 2, the web arrangement comprises a cross web 42 connecting the two electrically insulating sheaths to each other and an orthogonal web 44 connecting the lumen to the cross web. Preferably, the orthogonal web connecting the lumen to the electrical cords can be torn or be "unzipped" in a direction extending along the length of the cable assembly when the lumen is pulled away from the electrical cords by a force transverse to the direction of elongation. Similarly, the cross web can be torn to separate the two electrical cords. The webs can be made sufficiently thin to provide this tearable capability. If the webs were too thick, they would not tear properly or easily and would leave a ragged edge. Unzipping the lumen from the electrical cords at the source end can facilitate connection of the source ends of the lumen and the electrical cords to the source equipment, such as the electrical generator and the fluid pump or compressor. Similarly, unzipping the lumen from the electrical cords at the instrument end can facilitate connection of the instrument ends of the lumen and the electrical cords to the instrument.

The insulating sheath 20, 22, the lumen tubing 28, and the web arrangement 40 form a unitary tubular assembly comprising a continuum of flexible, plastic material. Suitable materials include polyvinyl chloride (PVC) or another flexible insulating plastic. The material should not be hard (not have a high durometer) and it should not be hydroscopic such that it holds so much water as to become slippery. The lumen tubing should be made of biocompatible material. The material cannot be water soluble or soluble in any fluid used for irrigation.

In a suitable exemplary embodiment, the web thickness is between 0.011 inch and 0.020 inch. The insulating sheath thickness is approximately 0.025 inch. The lumen tubing wall thickness is approximately 0.020 inch. It will be appreciated that these dimensions are merely exemplary of a suitable embodiment.

The cable assembly 10 is formed by a single extrusion process that ensures that the insulating sheaths 20, 22, the lumen tubing 28, and the web arrangement 40 are all formed as a single, unitary, integral assembly, with the sheaths surrounding the wires 16, 18. In a suitable extrusion process, plastic pellets, typically at room temperature, are placed into an extruder and heated above the melting temperature of the plastic. The extruder also pressurizes the plastic when in the molten stage. Once molten and at a high pressure, the plastic melt is forced through a die that has been cut to provide the desired profile of the cable assembly. The wires are also introduced into the die, as is known in the art. Once the melt has been forced through the die, it is cooled, preferably in a bath, to harden the plastic into the required shape and profile.

In another embodiment, the cable assembly can be formed from two materials co-extruded together. For example, one material can be used for the insulating sheaths of the electrical cord and another material can be used for the lumen tubing. The two materials are melted and fed through separate but closely arranged dies. Immediately upon exiting the dies, the materials are still in a molten state and are brought into contact. The two materials contact and melt together at the cross web or webs, thus resulting in a single, unitary, integral assembly. The assembly is then introduced into the cooling bath. Different materials can, in this manner, be selected to optimize the properties for the insulating sheaths and for the lumen tubing. Also in this manner, the lumen tubing can be provided in a different color from the electrical cord to allow a user to more readily distinguish the lumen visually from the electrical cord.

The electrical cords and the lumen(s) are preferably arranged in the most compact geometrical cross-section possible for the desired number of cords and lumens. In the embodiment illustrated in FIG. 2, two electrical cords 12, 14 and one lumen 24 are arranged in a triangular or pyramidal cross-sectional configuration. This configuration provides a compact arrangement that takes up a minimum amount of cross-sectional space and provides the feel of a single cable to the user. This cable assembly is suitable for use with a bipolar electrosurgical instrument requiring two electrical conductors and having one irrigation or aspiration line.

Figure 3:
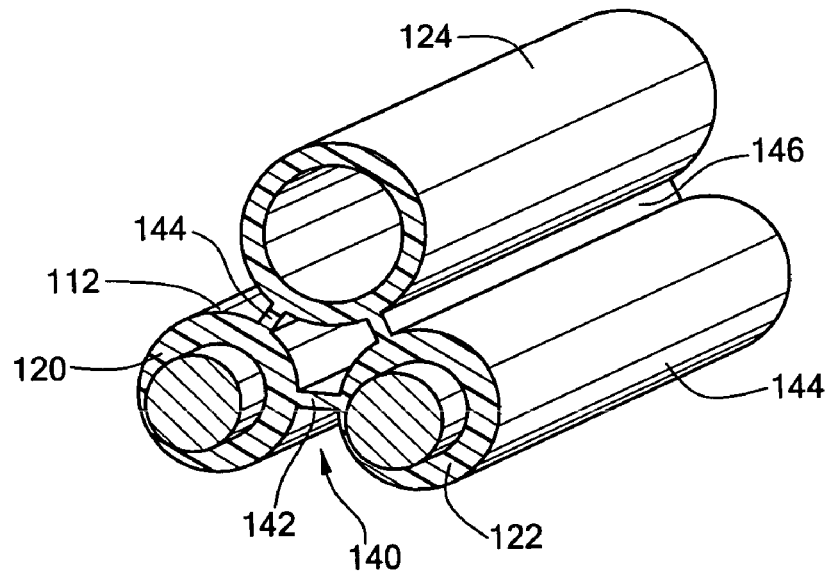
FIG. 3 is a partial cross-sectional view of a further embodiment of the cable assembly of the present invention.

FIG. 3 illustrates a further embodiment having an alternative interconnecting web arrangement 140. The insulating sheaths 120, 122 of two electrical cords 112, 114 are connected to each other with a cross web 142. A single lumen 124 is connected to each of the insulating sheaths by two further cross webs 144, 146. The three cross webs form a generally triangular arrangement. This arrangement is advantageous in that, if one web were severed unintentionally, the other two webs would still be available to hold the sheaths and tubing together.

Figure 4:
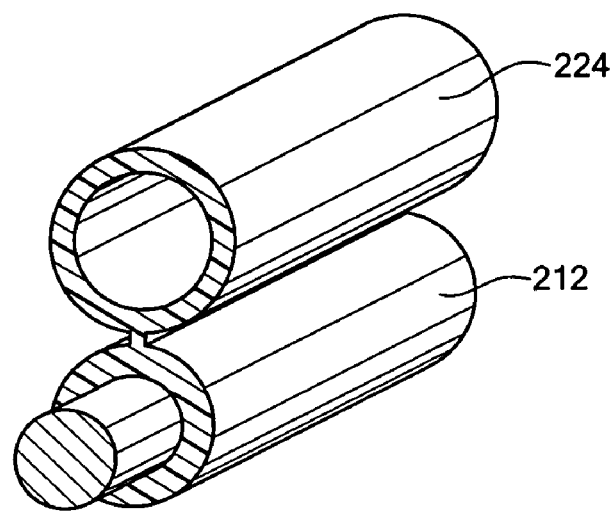
FIG. 4 is a partial cross-sectional view of a still further embodiment of the cable assembly of the present invention.

Other arrangements are possible. For example, the instrument connected to the end of the cable can be monopolar, in which case the cable requires only a single electrical conductor. FIG. 4 illustrates a suitable embodiment with one electrical cord 212 and one lumen 224 arranged in a linear or ribbon configuration. In another embodiment, the cable assembly can include further conductors for other potential uses, such as three conductors for use in connecting to a hand-switching device that can be either monopolar or bipolar, depending on the state of the switch.

Figure 5:
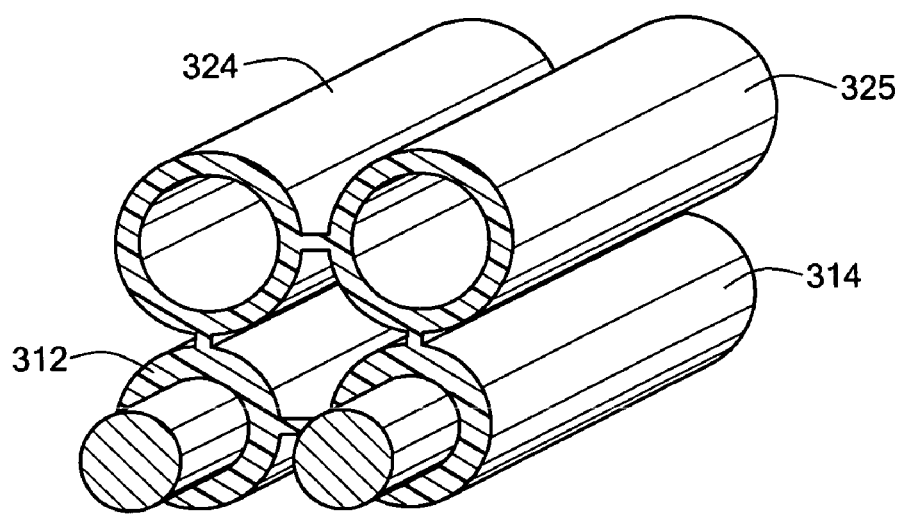
FIG. 5 is a partial cross-sectional view of a still further embodiment of the cable assembly of the present invention.

In another embodiment, the cable assembly includes two electrical conducting wires 312, 314 and two irrigation lumens 324, 325. See FIG. 5. The two electrical cords and two lumens are arranged in a rectangular cross-sectional configuration. In this embodiment, the irrigation lumens are isolated from each other to allow the infusion of two separate fluids or to allow for connection to an instrument that has two irrigating or aspirating lines, such as dual irrigating forceps. Two isolated irrigation lines are required for dual irrigating forceps to eliminate the potential of the electrical connection being made through the saline instead of between the bipolar forceps tines through the tissue.

The invention is not to be limited by what has been particularly shown and described, except as indicated by the appended claims.

What is claimed is:

1. A cable assembly for interconnecting an electrosurgical instrument and source equipment to provide electrical current from the source equipment to the instrument and fluid transfer between the electrosurgical instrument and the source equipment, the cable assembly comprising:

a unitary tubular assembly comprising:

at least two elongated hollow tubes extending between a source end and an instrument end, a first tube of the two tubes comprising a lumen, the interior of the lumen comprising a fluid flow passage, a second tube of the two tubes comprising an insulating sheath for an electrically conducting cord, and a web arrangement interconnecting the two elongated hollow tubes along the length of the tubular assembly between the source end and the instrument end, the web arrangement having a thickness sufficient to allow the two elongated hollow tubes to be pulled apart upon application of a pulling force in a direction transverse to the direction of elongation of the tubular assembly, and wherein the unitary tubular assembly comprises a continuum of flexible plastic insulating material;

a bare electrically conducting wire disposed within the hollow interior of the second tube, the second tube fully encircling and contacting the circumference of the bare electrically conducting wire;

a fluid handling fitting on the source end of the lumen for fluid connection to fluid handling equipment and a fluid handling fitting on the instrument end of the lumen for fluid connection to the instrument; and an electrical fitting on the source end of the second tube for electrical connection to an electrical generator and an electrical fitting on the instrument end of the second tube for electrical connection to the instrument.

2. The cable assembly of claim 1, wherein:

the unitary tubular assembly further comprises a third elongated hollow tube, the third tube comprising a further insulating sheath for a further electrically conducting cord;

the first tube, the second tube, and the third tube are arranged in a generally triangular configuration in cross-section; and the first tube, the second tube, and the third tube are held in the generally triangular configuration by the web arrangement along lengths where the web arrangement is not pulled apart.

3. The cable assembly of claim 1, wherein:

the unitary tubular assembly further comprises a third elongated hollow tube, the third tube comprising a further insulating sheath for a further electrically conducting cord, and a fourth elongated hollow tube, the fourth tube comprising a further lumen, the interior of the further lumen comprising a fluid flow passage;

the first tube, the second tube, the third tube, and the fourth tube are arranged in a generally rectangular configuration in cross-section; and the first tube, the second tube, the third tube, and the fourth tube are held in the generally rectangular configuration by the web arrangement along lengths where the web arrangement is not pulled apart.

4. The cable assembly of claim 1, wherein:

the unitary tubular assembly further comprises a third elongated hollow tube, the third tube comprising a further insulating sheath for a further electrically conducting cord; and the web arrangement further comprises a cross web extending between the second tube and the third tube, and a further web orthogonal to the cross web extending between the cross web and the first tube.

5. The cable assembly of claim 1, wherein:

the unitary tubular assembly further comprises a third elongated hollow tube, the third tube comprising a further insulating sheath for a further electrically conducting cord; and the web arrangement further comprises three cross webs extending between the first tube and the second tube, between the second tube and the third tube, and between the first tube and the third tub, the cross webs having a generally triangular cross-sectional configuration.

6. The cable assembly of claim 1, wherein the continuum of flexible plastic insulating material comprises polyvinyl chloride.

7. The cable assembly of claim 1, wherein the continuum of flexible plastic insulating material comprises a first plastic material forming the first tube and a second plastic material forming the second tube, the first plastic material and the second plastic material integrally solidified together within the web arrangement.

8. The cable assembly of claim 1, wherein the continuum of flexible plastic insulating material comprises a first plastic material forming the first tube and a second plastic material forming the second tube, the first plastic material and the second plastic material integrally solidified together within the web arrangement, the first material having a first color and the second material having a second color visually distinguishable from the first color.

9. The cable assembly of claim 1, wherein the unitary tubular assembly comprises an integrally extruded element between the source end and the instrument end.

10. The cable assembly of claim 1, wherein the fluid handling fitting on the instrument end of the lumen comprises a luer taper fitting.

* * * * *